United States Patent

Lund et al.

[11] Patent Number: 5,958,082
[45] Date of Patent: Sep. 28, 1999

[54] GARMENTS WITH CONSIDERABLE VARIATION IN ABRASION LEVEL

[75] Inventors: Henrik Lund, Copenhagen N; Lisbeth Kalum, Copenhagen ø, both of Denmark

[73] Assignee: Novo Nordisk A/S, Bagsvaerd, Denmark

[21] Appl. No.: 08/872,437

[22] Filed: Jun. 10, 1997

[30] Foreign Application Priority Data

Nov. 13, 1996 [DK] Denmark ................... 1276/96

[51] Int. Cl.$^6$ .................................. D06M 16/00
[52] U.S. Cl. .................. 8/102; 8/107; 8/114; 8/138; 8/401; 435/263
[58] Field of Search ............... 8/102, 107, 110, 8/111, 158, 159, 138, 114, 401; 435/263

[56] References Cited

FOREIGN PATENT DOCUMENTS

| 0 307 564 | 3/1989 | European Pat. Off. . |
|---|---|---|
| WO 90/07569 | 7/1990 | WIPO . |
| WO 95/09225 | 4/1995 | WIPO . |
| WO 96/29397 | 9/1996 | WIPO . |

*Primary Examiner*—Alan Diamond
*Attorney, Agent, or Firm*—Steve T. Zelson, Esq.; Reza Green, Esq.

[57] ABSTRACT

Garment, e.g. a new pair of jeans, made from dyed twill fabric and having localised variations in the colour density of the fabric providing the jeans with a stone-washed or abraded look corresponding to a delta remission value ($\Delta R$) higher than 11, and a reflection of a first area of the jeans fabric of less than 12%, the reflection and $\Delta R$ value being determined by a) measuring the reflection of the first and a second area of the fabric at a wavelength of 420 nm using a reflectometer having a measuring diaphragm with a diametrical dimension of 27 mm, the first area being located within the area of the upper half of the zipper cover visibly having the highest colour density (i.e. being relatively more coloured), and the second area being located at least about 5 cm from any stitching present on the jeans, b) expressing the reflection in % related to a white standard (100% reflection), and c) calculating the $\Delta R$ value as the difference between the % reflection of the first and the second area, respectively; and a process for the manufacturing of such garments.

17 Claims, No Drawings

SEQUENCE LISTING

<160> NUMBER OF SEQ ID NOS: 2

<210> SEQ ID NO 1
<211> LENGTH: 1174
<212> TYPE: DNA
<213> ORGANISM: Thielavia terrestris

<400> SEQUENCE: 1
gagcagcacc cctcaagctg tacagtttcc accccgctct cttttcttcg gcccccagga      60

-continued

```
tgcgctctac tcccgttctt cgcacaaccc tggccgctgc acttcctctg gtcgcctccg      120
cggccagtgg cagtggccag tccacgagat actgggactg ctgcaagccg tcgtgcgctt      180
ggcccgggaa ggccgccgtc agccaaccgg tctacgcgtg cgatgccaac ttccagcgcc      240
tgtccgactt caatgtccag tcgggctgca acggcggctc ggcctactcc tgcgccgacc      300
agactccctg gcggtgaac  gacaatctcg cctacggctt cgccgcgacg agcatcgccg      360
gcgggtccga atcctcgtgg tgctgcgcct gctacgcgct caccttcact ccggtcccg      420 tcgccggcaa gacaatggtg gtgcagtcaa cgagcactgg cggcgacctg gaagtaacc      480 agttcgatat cgccatgccc ggcggcggcg tgggcatctt caacggctgc agctcgcagt      540
tcggcggcct ccccggcgct caatacggcg gcatttcgtc gcgcgaccag tgcgattcct      600
tccccgcgcc gctcaagccc ggctgccagt ggcggtttga ctggttccag aacgccgaca      660
acccgacgtt cacgttccag caggtgcagt gccccgccga atcgttgcc cgctccggct       720 gcaagcgcaa cgacgactcc agcttccccg tcttcacccc cccaagcggt ggcaacggtg      780
gcaccgggac gcccacgtcg actgcgcctg gtcgggcca  gacgtctccc ggcggcggca      840
gtggctgcac gtctcagaag tgggctcagt gcggtggcat cggcttcagc ggatgcacca      900
cctgtgtctc tggcaccacc tgccagaagt tgaacgacta ctactcgcag tgcctctaaa     960
cagcttttcg cacgaggtgg cgggacggag caaggagacc gtcaacttcg tcatgcatat    1020
tttttgagcg ctcaatacat acataacctt cgattcttgt acatagcacg ccggtacaca    1080
tctcacaccg actttggggg cggaatcagg cccgttttaa aaaaaaaaaa aaaaaaaaaa    1140
aaaaaaaaaa aaaaaaaaaa aaaaaaaaaa aaaa                                 1174
```

<210> SEQ ID NO 2
<211> LENGTH: 299
<212> TYPE: PRT
<213> ORGANISM: Thielavia terrestris

<400> SEQUENCE: 2

```
Met Arg Ser Thr Pro Val Leu Arg Thr Thr Leu Ala Ala Ala Leu Pro
 1               5                  10                  15

Leu Val Ala Ser Ala Ala Ser Gly Ser Gly Gln Ser Thr Arg Tyr Trp
             20                  25                  30

Asp Cys Cys Lys Pro Ser Cys Ala Trp Pro Gly Lys Ala Val Ser
             35                  40                  45

Gln Pro Val Tyr Ala Cys Asp Ala Asn Phe Gln Arg Leu Ser Asp Phe
 50                  55                  60

Asn Val Gln Ser Gly Cys Asn Gly Gly Ser Ala Tyr Ser Cys Ala Asp
 65                  70                  75                  80

Gln Thr Pro Trp Ala Val Asn Asp Asn Leu Ala Tyr Gly Phe Ala Ala
             85                  90                  95

Thr Ser Ile Ala Gly Gly Ser Glu Ser Ser Trp Cys Cys Ala Cys Tyr
            100                 105                 110

Ala Leu Thr Phe Thr Ser Gly Pro Val Ala Gly Lys Thr Met Val Val
            115                 120                 125

Gln Ser Thr Ser Thr Gly Gly Asp Leu Gly Ser Asn Gln Phe Asp Ile
            130                 135                 140

Ala Met Pro Gly Gly Gly Val Gly Ile Phe Asn Gly Cys Ser Ser Gln
145                 150                 155                 160

Phe Gly Gly Leu Pro Gly Ala Gly Tyr Gly Gly Ile Ser Ser Arg Asp
            165                 170                 175

Gln Cys Asp Ser Phe Pro Ala Pro Leu Lys Pro Gly Cys Gln Trp Arg
```

-continued

```
                      180                 185                 190
Phe Asp Trp Phe Gln Asn Ala Asp Asn Pro Thr Phe Thr Phe Gln Gln
            195                 200                 205
Val Gln Cys Pro Ala Glu Ile Val Ala Arg Ser Gly Cys Lys Arg Asn
            210                 215                 220
Asp Asp Ser Ser Phe Pro Val Phe Thr Pro Pro Ser Gly Gly Asn Gly
225                 230                 235                 240
Gly Thr Gly Thr Pro Thr Ser Thr Ala Pro Gly Ser Gly Gln Thr Ser
                245                 250                 255
Pro Gly Gly Gly Ser Gly Cys Thr Ser Gln Lys Trp Ala Gln Cys Gly
            260                 265                 270
Gly Ile Gly Phe Ser Gly Cys Thr Thr Cys Val Ser Gly Thr Thr Cys
            275                 280                 285
Gln Lys Leu Asn Asp Tyr Tyr Ser Gln Cys Leu
            290                 295
```

GARMENTS WITH CONSIDERABLE VARIATION IN ABRASION LEVEL

CROSS-REFERENCE TO RELATED APPLICATIONS

This application claims priority under 35 U.S.C. 119 of Danish application serial no. 1276/96 filed Nov. 13, 1996, the contents of which are fully incorporated herein by reference.

The present invention relates to a new garment, e.g., a new pair of jeans made from dyed twill fabric and having a special worn look, i.e. a considerable variation in the abrasion level, and to a process for providing such a garment.

BACKGROUND OF THE INVENTION

The popularity of denim fabrics among consumers of all ages has been well documented by sales in a large number of countries throughout the world.

Denim is cotton cloth. A conventional dyestuff for denim is the dye indigo having a characteristic blue colour, the indigo-dyed denim cloth having the desirable characteristic of alteration of dyed threads with white threads which upon normal wear and tear gives denim a white on blue appearance. A popular look for denim is the stonewashed look.

Traditionally stonewashing has been performed by laundering the denim material or garment in the presence of pumice stones which results in fabric having a faded or worn appearance with the desired white on blue contrast appearance described above. This stonewashed look primarily consists of removal of dye in a manner to yield a material with areas which are lighter in colour, while maintaining the desirable white on blue contrast, and a material which is softer in texture.

Enzymes, particularly cellulases, are currently used in processing dyed twill fabric, especially denim. In particular cellulolytic enzymes or cellulases have been used as a replacement for or in combination with pumice stones for the traditional "stonewashing" process sued to give denim a faded look. Use of enzymes to stonewash has become increasingly popular because use of stones alone have several disadvantages. For example, stones used in the process cause wear and tear on the machinery, they cause environmental waste problems due to the grit produced and result in high labour costs associated with the manual removal of the stones from pockets of garments. Consequently, reduction or elimination of stones in the wash may be desirable. Contrary to the use of pumice stones, enzymes, in particular cellulases, are safe for the machinery, result in little or no waste problem and drastically reduce labour costs.

A major proportion of the denim garments sold today are treated to impart some aesthetic or fashionable character to the fabric or garment, often a worn or abraded look.

Examples of widely used means of imparting an aesthetically pleasing look or a fashionably faded or worn look to denim fabrics or garments are the processes of stonewashing, ice washing, acid washing, sand blasting, bleaching, overdying, i.e. mechanical or chemical processes.

It is an object of the present invention to achieve a new garment with a special abraded look, i.e. a garment with a considerable variation in the abrasion level, in which the abraded look near stitchings are different from the abraded look far from stitchings.

SUMMARY OF THE INVENTION

The present invention relates to a new pair of jeans made from dyed twill fabric and having localised variations in the colour density of the fabric providing the jeans with a stone-washed or abraded look, wherein the variation corresponds to a delta remission value ($\Delta R$) higher than 11, and the reflection of a first area of the jeans fabric is less than 12%, the reflection and $\Delta R$ value being determined by a. measuring the reflection of the first and a second area of the fabric at a wavelength of 420 nm using a reflectometer having a measuring diaphragm with a diametrical dimension of 27 mm, the first area being located within the area of the upper half of the zipper cover visibly having the highest colour density (i.e. being relatively more coloured), and the second area being located at least about 5 cm from any stitching present on the jeans, b. expressing the reflection in % related to a white standard (100% reflection), and c. calculating the $\Delta R$ value as the difference between the % reflection of the first and the second area, respectively.

The present invention also relates to a process for providing a new pair of jeans made from dyed twill fabric and having localised variations in the colour density of the fabric providing the jeans with a stone-washed or abraded look corresponding to a delta remission value ($\Delta R$) higher than 11, and the reflection of a first area of the jeans is less than 12%, the reflection and the $\Delta R$ value being determined by a. measuring the reflection of a first and a second area of the fabric at a wavelength of 420 nm using a reflectometer having a measuring diaphragm with a diametrical dimension of 27 mm, the first area being located within the area of the upper half of the zipper cover visibly having the highest colour density (i.e. being relatively more coloured), and the second area being located at least about 5 cm from any stitching present on the jeans, b. expressing the reflection in % related to a white standard (100% reflection), and c. calculating the $\Delta R$ value as the difference between the % reflection of the first and the second area, respectively, the process comprising the steps of i. selecting the desired textile cutting pattern for jeans garment, ii. positioning the pattern onto newly manufactured dyed twill fabric, iii. cutting the jeans garment parts, iv. sowing the pair of jeans, v. optionally subjecting the pair of jeans to a desizing treatment, vi. subjecting the pair of jeans to an abrasion treatment with an efficient amount of a cellulolytic enzyme in an aqueous medium essentially free of bleaching chemicals.

The abrasion treatment may be a one-cycle treatment or the abrasion treatment may be done in more than one cycle.

After the treatment with the cellulolytic enzyme the pair of jeans (or the garment in question) may be subjected to any additional finishing step such as bleaching, treatment with softener, afterwash with alkali and/or detergent, treatment with optical brightener etc.

DETAILED DESCRIPTION OF THE INVENTION

Garments

According to the invention any garment made of dyed twill fabric supplied with a zipper cover, e.g. jeans, jackets, coats, skirts, waistcoats, dresses, in particular jeans, may get the abraded look described in this invention.

According to the invention the wording zipper cover is intended to include any cover that covers a place on the garment which can be opened/closed such as a zipper, one or more buttons, velcro, etc.

Dyed Fabric

The invention may be applied to any dyed twill fabric known in the art, in particular to natural fabrics.

The invention is most beneficially applied to cellulose-containing fabrics, such as cotton, viscose, rayon, ramie, linen, Tencel, or mixtures thereof, or mixtures of any of these fibres, or mixtures of any of these fibres together with synthetic fibres. In particular, the fabric is denim.

The fabric may be dyed with any dye known in the art, in particular with a dye selected from the group consisting of sulfur dyes, direct dyes, naphthol dyes, reactive dyes and vat dyes.

A preferred embodiment of the invention is ring-dyeing of the warp with a vat dye such as indigo, or an indigo-related dye such as thioindigo. The fabric may also be dyed with more than one dye, e.g., first with a sulphur dye and then with an indigo dye, or vice versa.

In another preferred embodiment of the invention, the fabric is an indigo-dyed denim with a sulphur-bottom or with a sulphur-top, (i.e. the denim is first dyed with a sulphur dye and then with an indigo dye, or vice versa).

The process

The look of the twill fabric as described in the present invention may be obtained by various processes; a preferred process comprises the following steps:

i. selecting the desired textile cutting pattern for the garment, e.g., the jeans, ii. positioning the pattern onto newly manufactured dyed twill fabric, iii. cutting the garment, e.g., the jeans parts, iv. sowing the piece of garment, e.g., the pair of jeans, v. optionally subjecting the piece of garment, e.g., the pair of jeans to a desizing treatment, vi. subjecting the garment, e.g., the pair of jeans to an abrasion treatment with an efficient amount of a cellulolytic enzyme in an aqueous medium essentially free of bleaching chemicals.

The skilled person in the art will realise that the effective amount of a cellulolytic enzyme will vary depending upon a number of well understood parameters, including the purity and the specific activity of the cellulase, the contact time, the pH, the temperature of the aqueous process medium, the presence of abrasives (pumice, perlite, diatomaceous earth, ECO-balls) and the machinery used for fabric (e.g. denim) wet processing:

Machinery for fabric wet processing

When processing fabric, in particular denim, the mechanical action is a very important parameter to consider in order to obtain the desired abrasion level. The machine design plays an important role in getting the desired abrasion level. Abrasion comes from fabric-to-fabric, fabric-to-metal or fabric-to-stone/abrasive contact.

The machines function primarily as a washer. Since denim processing started in industrial laundries most of the equipment has been an adaptation of washing machines. Two main categories exist today: Washer Extractor and Barrel Machines.

Washer extractors are characterized by having an internal rotating drum which makes extraction possible, and there are two basic designs of washer extractor: Front-loaded and side washers. Cylinder design vary widely. The diameter of the cylinder in a front load washer extractor is generally greater than the length of the cylinder. It rotates along its horizontal axis and is loaded through an opening in the end. Side-loading machines are similar to front loaders in the basic design principles, however, the cylinder is longer than its diameter, it rotates along its horizontal axis and is loaded through openings in the side. Baffles are protruding from the inside of the drum which help keep the garments moving for better abrasion. The garments are lifted with the help of the baffles to the top of the drum and then fall back into the wash liquor.

Barrel (or hexagonal) washers are designed with only one drum. The machine is designed especially for stonewashing jeans. The mechanical effect, from both fabric-to-fabric and fabric-to-drum contact, is very high resulting in a very effective stonewash.

According to the present invention a Barrel washer is preferred.

The desizing and abrasion process

In a preferred process of the invention, conventional desizing enzymes, in particular amylolytic enzymes, are used in order to remove starch-containing size.

Therefore, an amylolytic enzyme, preferably an α-amylase, may be added during the process of the invention. Conventionally, bacterial α-amylases are used for the desizing, e.g. an α-amylases derived from a strain of Bacillus, particularly a strain of *Bacillus licheniformis,* a strain of *Bacillus amyloliquefaciens,* or a strain of *Bacillus stearothermophilus;* or mutants thereof. Examples of suitable commercial α-amylase products are Termamyl™, Aquazym™ Ultra and Aquazym™ (available from Novo Nordisk A/S, Denmark). However, also fungal α-amylases can be used. Examples of fungal α-amylases are those derived from a strain of Aspergillus. Other useful α-amylases are the oxidation-stable α-amylase mutants disclosed in WO 95/21247.

The amylolytic enzyme may be added in amounts conventionally used in desizing processes, e.g. corresponding to an α-amylase activity of from about 100 to about 10,000 KNU/l. Also, in the process according to the present invention, 1–10 mM of $Ca^{++}$ may be added as a stabilizing agent.

In the present context, the term "cellulolytic" enzyme refers to an enzyme which catalyses the degradation of cellulose to glucose, cellobiose, triose and other cello-oligosaccharides.

In the present context the term "cellulolytic" enzyme is understood to include a mature protein or a precursor form thereof or a functional fragment thereof which essentially has the activity of the full-length enzyme. Furthermore, the term "cellulolytic" enzyme is intended to include homologues or analogues of said enzyme.

Preferably, the cellulolytic enzyme to be used in the present invention is a monocomponent (recombinant) cellulase, i.e. a cellulase essentially free from other proteins or cellulase proteins. A recombinant cellulase component may be cloned and expressed according to standard techniques conventional to the skilled person.

In a preferred embodiment of the invention, the cellulase to be used in the method is an endoglucanase (EC 3.2.1.4), preferably a monocomponent (recombinant) endoglucanase.

Preferably, the cellulase is a microbial cellulase, more preferably a bacterial or fungal cellulase.

Examples of bacterial cellulases are cellulases derived from or producible by bacteria from the group of genera consisting of Pseudomonas or Bacillus, in particular *Bacillus lautus.*

The cellulase or endoglucanase may be an acid, a neutral or an alkaline cellulase or endoglucanase, i.e. exhibiting maximum cellulolytic activity in the acid, neutral or alkaline range, respectively.

Accordingly, a useful cellulase is an acid cellulase, preferably a fungal acid cellulase, which is derived from or producible by fungi from the group of genera consisting of Trichoderma, Actinomyces, Myrothecium, Aspergillus, or Botrytis, in particular *Trichoderma viride, Trichoderma reesei, Trichoderma longibrachiatum, Myrothecium verrucaria, Aspergillus niger, Aspergillus oryzae,* or *Botrytis cinerea.*

Another useful cellulase or endoglucanase is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium, in particular *Humicola insolens, Fusarium oxysporum, Myceliopthora thermophila,* or *Cephalosporium sp.,* preferably from the group of species consisting of *Humicola insolens,* DSM 1800, *Fusarium oxysporum,* DSM 2672, *Myceliopthora thermophila,* CBS 117.65, or *Cephalosporium sp.,* RYM-202.

A preferred example of a native or parent cellulase is an alkaline endoglucanase which is immunologically reactive with an antibody raised against a highly purified 43 kD endoglucanase derived from *Humicola insolens,* DSM 1800, or which is a derivative of the 43 kD endoglucanase exhibiting cellulase activity.

Other examples of useful cellulases are variants having, as a parent cellulase, a cellulase of fungal origin, e.g. a cellulase derivable from a strain of the fungal genus Humicola, Trichoderma or Fusarium.

A preferred useful monocomponent cellulase is the species *Thielavia terrestris,* in particular *Thielavia terrestris,* NRRL 8126, obtainable as described in WO 96/29397, and having the amino acid sequence listed in SEQ ID 2.

A preferred cellulolytic enzyme according to the invention is monocomponent endoglucanase encoded by a DNA construct comprising the DNA sequence listed in SEQ ID 1 or the DNA sequence obtainable from the plasmid in *Saccharomyces cerevisiae,* DSM 10081 (described in WO 96/29397), or an analogue of the DNA sequence listed in SEQ ID 1 or the DNA sequence obtainable from the plasmid in *Saccharomyces cerevisiae,* DSM 10081, which i. is homologous, preferably at least 75% homologous, with the DNA sequence shown in SEQ ID 1 or the DNA sequence obtainable from the plasmid in *Saccharomyces cerevisiae,* DSM 10081,
  ii. hybridizes with the same nucleotide probe as the DNA sequence shown in SEQ ID 1 or the DNA sequence obtainable from the plasmid in *Saccharomyces cerevisiae,* DSM 10081 when the hybridization is performed in a solution containing 5×SSC at 45° C. and the hybrids are washed in a solution comprising 2×SSC at 50° C.,
  iii. encodes a polypeptide which is homologous, preferably at least 70% homologous, with the polypeptide encoded by a DNA sequence comprising the DNA sequence shown in SEQ ID 1 or the DNA sequence obtainable from the plasmid in *Saccharomyces cerevisiae,* DSM 10081,
  iv. encodes a polypeptide which is immunologically reactive with an antibody raised against the purified endoglucanase encoded by the DNA sequence shown in SEQ ID 1 or the DNA sequence obtainable from the plasmid in *Saccharomyces cerevisiae,* DSM 10081.

As stated above the amount of cellulolytic enzyme needed to achieve the desired look depends on many factors, but according to the invention the concentration of the cellulolytic enzyme in the aqueous medium may be 0.001–50 mg of enzyme protein per g of fabric, preferably 0.005–25 mg of enzyme protein per g of fabric, more preferably 0.01–5 mg of enzyme protein per g of fabric.

It is at present advised that a suitable liquor/textile ratio may be in the range of from about 20:1 to about 1:1, preferably in the range of from about 15:1 to about 2:1.

In conventional desizing and "stone-washing" processes, the reaction time is usually in the range of from about 10 min to about 8 hours. Preferably the reaction time is within the range of from about 10 to about 120 minutes.

The pH of the reaction medium greatly depends on the enzyme in question. Preferably the process of the invention is carried out at a pH in the range of from about pH 3 to about pH 11, preferably in the range of from about pH 4 to about pH 8, or within the range of from about pH 4.5 to about pH 5.5.

The temperature of the reaction medium also greatly depends on the enzyme in question. Normally a temperature in the range of from 10°–80° C. will be used, preferably a temperature in the range of from 50°–70° C. will be used, more preferably a temperature in the range of from 60°–65° C. will be used. Sometimes the temperature used for the desizing process and the abrasion process will be the same, but normally they will be different as shown in Example 1 of the present invention.

A buffer may be added to the reaction medium to maintain a suitable pH for the enzymes used. The buffer may suitably be a phosphate, borate, citrate, acetate, adipate, triethanolamine, monoethanolamine, diethanolamine, carbonate (especially alkali metal or alkaline earth metal, in particular sodium or potassium carbonate, or ammonium and HCl salts), diamine, especially diaminoethane, imidazole, or amino acid buffer.

The process of the invention may be carried out in the presence of conventional textile finishing agents, including wetting agents, polymeric agents, dispersing agents, etc.

A conventional wetting agent may be used to improve the contact between the substrate and the enzymes used in the process. The wetting agent may be a nonionic surfactant, e.g. an ethoxylated fatty alcohol. A very useful wetting agent is an ethoxylated and propoxylated fatty acid ester such as Berol 087 (product of Akzo Nobel, Sweden).

Examples of suitable polymers include proteins (e.g. bovine serum albumin, whey, casein or legume proteins), protein hydrolysates (e.g. whey, casein or soy protein hydrolysate), polypeptides, lignosulfonates, polysaccharides and derivatives thereof, polyethylene glycol, polypropylene glycol, polyvinyl pyrrolidone, ethylene diamine condensed with ethylene or propylene oxide, ethoxylated polyamines, or ethoxylated amine polymers.

The dispersing agent may suitably be selected from nonionic, anionic, cationic, ampholytic or zwitterionic surfactants. More specifically, the dispersing agent may be selected from carboxymethylcellulose, hydroxypropylcellulose, alkyl aryl sulphonates, long-chain alcohol sulphates (primary and secondary alkyl sulphates), sulphonated olefins, sulphated monoglycerides, sulphated ethers, sulphosuccinates, sulphonated methyl ethers, alkane sulphonates, phosphate esters, alkyl isothionates, acylsarcosides, alkyltaurides, fluorosurfactants, fatty alcohol and alkylphenol condensates, fatty acid condensates, condensates of ethylene oxide with an amine, condensates of ethylene oxide with an amide, sucrose esters, sorbitan esters, alkyloamides, fatty amine oxides, ethoxylated monoamines, ethoxylated diamines, alcohol ethoxylate and mixtures thereof. A very useful dispersing agent is an alcohol ethoxylate such as Berol 08 (product of Akzo Nobel, Sweden).

Conventional finishing agents that may be present in a process of the invention include, but are not limited to pumice stones and/or perlite. Perlite is a naturally occurring volcanic rock. Preferably, heat expanded perlite may be used.

If pumice stones are used it will normally be included in an amount of 0–80% relative to the amount which is conventionally used for stonewashing jeans with pumice in a conventional stonewashing process.

In a preferred embodiment of the invention the process is a combi-process, i.e. the process is a combined desizing and abrasion process.

Cellulolytic Activity

The cellulytic activity may be measured in endocellulase units (ECU), determined at pH 7.5, with carboxymethyl cellulose (CMC) as substrate.

The ECU assay quantifies the amount of catalytic activity present in the sample by measuring the ability of the sample to reduce the viscosity of a solution of carboxymethylcellulose (CMC). The assay is carried out at 40° C.; pH 7.5; 0.1M phosphate buffer; time 30 min; using a relative enzyme standard for reducing the viscosity of the CMC Hercules 7 LFD substrate; enzyme concentration approx. 0.15 ECU/ml. The arch standard is defined to 8200 ECU/g.

Amylolytic Activity

The amylolytic activity may be determined using potato starch as substrate. This method is based on the breakdown of modified potato starch by the enzyme, and the reaction is followed by mixing samples of the starch/enzyme solution with an iodine solution. Initially, a blackish-blue colour is formed, but during the break-down of the starch the blue colour gets weaker and gradually turns into a reddish-brown, which is compared to a coloured glass standard.

One Kilo Novo alfa Amylase Unit (KNU) is defined as the amount of enzyme which, under standard conditions (i.e. at 37° C. +/−0.05; 0.0003M $Ca^{2+}$; and pH 5.6) dextrinizes 5.26 g starch dry substance Merck Amylum solubile.

Reflection measurements

The reflection measurements which define the look of the fabric according to the invention are done at a wavelength of 420 nm using a reflectometer having a measuring diaphragm with a diametrical dimension of 27 mm. All reflection measurements are expressed in % related to a white standard (100% reflection).

The white standard used was a Datacolor international serial no. 2118 white calibration standard.

For calibration purposes a black standard was also used (no. TL-4-405).

The invention is further illustrated in the following example which is not intended to be in any way limiting to the scope of the invention as claimed.

EXAMPLE 1

Abraded leans look
Experimental
Apparatus: Barrel washer, Diameter: 1 m, rpm: 29
Liquid volume: 47 l
Fabric: 5.7 kg Denim fabric, indigo dyed Prior art jeans no 1, 2 and 3 are commercial jeans with the look stated under "Note" in the Table below.
Enzyme: *Thielavia cellulase,* 2410 ECU/g
Desizing: 2.5 g/l phosphate buffer, pH 7 210 ml Aquazyme 120 L 10 min, 55° C.
Abrasion: 1 g/l citrate buffer, pH 5 29 ml *Thielavia cellulase* (15 ECU/g textile) 60 min, 65° C.
Inactivation: 1 g/l sodium carbonate 15 min. 80° C.
Rinses: Three rinse cycles of 5 min in 47 l tap water
Evaluation: Reflection measurements were performed as described above.
Results The *Thielavia cellulase* treated fabric is compared to three commercial pair of jeans (Prior art no 1, 2 and 3). The results from the reflection measurements on the zipper cover and on the middle of the jeans (mean value of 10 or 20 measurements determined at least five cm from any stitching) are shown in the following table:

| Jeans | Reflection on zipper cover | Reflection on the middle of the jeans | ΔR | Note |
|---|---|---|---|---|
| Invention | 8.81% | 21.31% | 12.5 | — |
| Prior art, no 1 | 36.00% | 50.38% | 14.38 | Bleached |
| Prior art, no 2 | 17.46% | 30.04% | 12.58 | Mild bleach |
| Prior art, no 3 | 8.85% | 16.39% | 7.54 | High abrasion, mild bleach |

The jeans abraded with the *Thielavia cellulase* results in an abraded look where the dark areas on stitching and on the zipper cover are maintained. Traditionally bleached jeans impart the jeans with a higher reflection, but at the expense of lost contrast on stitching etc.

It can be seen from the Table that in the prior art cases when the reflection on the zipper cover is below 12% abrasion units, the ΔR value is below 11.

The surprising appearance of the jeans produced according to the invention results in a highly abraded look, while maintaining the dark patch on the zipper cover.

We claim:

1. A process for providing a new pair of jeans made from dyed twill fabric and having localised variations in the colour density of the fabric providing the jeans with a stone-washed or abraded look corresponding to a delta remission value (ΔR) higher than 11 and a reflection of a first area of the jeans fabric less than 12%, the reflection and the ΔR value being determined by
   a. measuring the reflection of a first and a second area of the fabric at a wavelength of 420 nm using a reflectometer having a measuring diaphragm with a diametrical dimension of 27 mm, the first area being located within the area of the upper half of the zipper cover visibly having the highest colour density, and the second area being located at least about 5 cm from any stitching present on the jeans,
   b. expressing the reflection in % related to 100% reflection, and
   c. calculating the ΔR value as the difference between the % reflection of the first and the second area, respectively, the process comprising the steps of
   i. sewing a pair of jeans from newly manufactured dyed twill fabric, and
   ii. subjecting the pair of jeans to an abrasion treatment with an efficient amount of a cellulolytic enzyme in an aqueous medium essentially free of bleaching chemicals, wherein said cellulolytic enzyme is a monocomponent endoglucanase obtainable from a fungal strain belonging to the species *Thielavia terrestris* or an analogue of said monocomponent endoglucanase.

2. The process according to claim 1, wherein the abrasion treatment further includes treatment with pumice in an amount of 0–80% relative to the amount which is conventionally used for stonewashing jeans with pumice in a conventional stonewashing process.

3. The process according to claim 1, wherein the ΔR value is higher than 12.

4. The process according to claim 1, wherein the % reflection of the first area is less than 11.

5. The process according to claim 1, wherein the pH of the aqueous medium is from about 4 to about 8.

6. The process according to claim 1, wherein the treatment is carried out at a temperature below 75° C.

7. The process according to claim 1, wherein the species is *Thielavia terrestris*, NRRL 8126.

8. The process according to claim 1, wherein the monocomponent endoglucanase has the amino acid sequence listed in SEQ ID NO:2.

9. The process according to claim 1, wherein the monocomponent endoglucanase is encoded by a DNA construct comprising a DNA sequence selected from the group consisting of: (a) the DNA sequence listed in SEQ ID NO: 1 or an analogue thereof and (b) the DNA sequence obtainable from the plasmid in *Saccharomyces cerevisiae*, DSM 10081 or an analogue thereof, wherein said analogue
   i. is at least 75% homologous with the DNA sequence shown in SEQ ID NO: 1 or the DNA sequence obtainable from the plasmid in *Saccharomyces cerevisiae*, DSM 10081 or
   ii. hybridizes with the same nucleotide probe as the DNA sequence shown in SEQ ID NO: 1 or the DNA sequence obtainable from the plasmid in *Saccharomyces cerevisiae*, DSM 10081 when the hybridization is performed in a solution containing 5 ×Standard Saline Citrate (SSC) at 45° C. and the hybrids are washed in a solution comprising 2×SSC at 50° C., or
   iii. encodes a polypeptide which is at least 70% homologous with a polypeptide encoded by a DNA sequence comprising the DNA sequence shown in SEQ ID NO:1 or the DNA sequence obtainable from the plasmid in *Saccharomyces cerevisiae*, DSM 10081, or
   iv. encodes a polypeptide which is immunologically reactive with an antibody raised against the purified endoglucanase encoded by the DNA sequence shown in SEQ ID NO:1 or the DNA sequence obtainable from the plasmid in *Saccharonyces cerevisiae*, DSM 10081.

10. A process according to claim 11 wherein the jeans are indigo-dyed denim with a sulphur-bottom or a sulphur-top.

11. A process according to claim 1, wherein a desizing treatment is combined with the abrasion treatment.

12. A new pair of jeans made from dyed twill fabric and having localised variations in the colour density of the fabric providing the jeans with a stone-washed or abraded look, wherein said jeans are produced using the method according to claim 11.

13. The pair of jeans according to claim 12, wherein the ΔR value is higher than 12.

14. The pair of jeans according to claim 12, wherein the warp of the jeans fabric is dyed with a dye selected from the group consisting of sulfur dyes, direct dyes, naphthol dyes, reactive dyes, and vat dyes.

15. The pair of jeans according to claim 14, wherein the fabric warp is dyed with indigo.

16. The pair of jeans according to claim 15 which is a pair of blue denim jeans.

17. The pair of jeans according to claim 16, wherein the % reflection of the first area is less than 11.

\* \* \* \* \*